US008629287B2

(12) United States Patent
Sukopp et al.

(10) Patent No.: US 8,629,287 B2
(45) Date of Patent: *Jan. 14, 2014

(54) PROCESS FOR THE SULFINYLATION OF A PYRAZOLE DERIVATIVE

(75) Inventors: Martin Sukopp, Mannheim (DE); Oliver Kuhn, Rosport (LU); Carsten Gröning, Mannheim (DE); Michael Keil, Freinsheim (DE); Jon J. Longlet, Nederland, TX (US)

(73) Assignee: BASF SE, Ludwigshafen (DE)

( * ) Notice: Subject to any disclaimer, the term of this patent is extended or adjusted under 35 U.S.C. 154(b) by 242 days.

This patent is subject to a terminal disclaimer.

(21) Appl. No.: 12/514,103

(22) PCT Filed: Nov. 5, 2007

(86) PCT No.: PCT/EP2007/061893
§ 371 (c)(1),
(2), (4) Date: May 8, 2009

(87) PCT Pub. No.: WO2008/055879
PCT Pub. Date: May 15, 2008

(65) Prior Publication Data
US 2010/0093822 A1   Apr. 15, 2010

Related U.S. Application Data

(60) Provisional application No. 60/865,178, filed on Nov. 10, 2006, provisional application No. 60/913,638, filed on Apr. 24, 2007.

(51) Int. Cl.
    *C07D 231/18* (2006.01)
(52) U.S. Cl.
    USPC ..................................................... 548/367.4
(58) Field of Classification Search
    None
    See application file for complete search history.

(56) References Cited

U.S. PATENT DOCUMENTS

| 4,724,095 | A | 2/1988 | Gresser |
| 5,618,945 | A * | 4/1997 | Casado et al. ............ 548/367.4 |
| 6,203,670 | B1 | 3/2001 | Forat et al. |
| 6,399,815 | B2 | 6/2002 | Suzuki |
| 2011/0190510 | A1 | 8/2011 | Sukopp et al. |

FOREIGN PATENT DOCUMENTS

| CN | 1 374 298 | 10/2002 |
| DE | 198 53 560 | 5/2000 |
| EP | 0 165 136 | 12/1985 |
| EP | 0 295 117 | 12/1988 |
| EP | 0 668 269 | 8/1995 |
| EP | 1 331 222 | 7/2003 |
| WO | WO 99/32439 | 7/1999 |
| WO | WO 01/30760 | 5/2001 |
| WO | WO 2008/055877 | 5/2008 |
| WO | WO 2008/055880 | 5/2008 |
| WO | WO 2009/068533 | 6/2009 |
| WO | WO 2010/037693 | 9/2009 |

OTHER PUBLICATIONS

International Search Report completed Mar. 19, 2008, in International Application No. PCT/EP2007/061893, filed Nov. 5, 2007.
International Preliminary Report on Patentability dated Feb. 20, 2008, from corresponding International Application No. PCT/EP2007/061893, filed Nov. 5, 2007.
Billard, Thierry, et al., "A New Equivalent of the CF3S(O)+ Cation. Synthesis of Trifluoromethanesulfinates andTrifluoromethanesulfinamides", Tetrahedron, 1999, p. 7243-7250, vol. 55.
Huilong, Yang et al., "Study on the Synthesis of Regent", Journal of Hebei University of Science and Technology, 2004, p. 69-73, vol. 25, No. 2.
Ren, Qing-Yun, et al., "Research Progress on Synthesis of Fipronil and its Main Intermediate", Chinese Journal of Pesticides, 2004, pp. 529-531, vol. 43, No. 12.
Wakselman, Claude, et al., "Aryltrifluoromethylsulfoxides: Sulfinylation of Aromatics by Triflinate Salts in Acid Medium", Synlett, 2001, p. 550-552, No. 4.
Roesky, H.W. et al., "Perfluoroalkansulfinsaeure-ester, -amide und isocyanate", Chem.Ber. 1974, p. 508-517, vol. 107.
Andrieux, C.P. et al., "Outer-Sphere and Inner-Sphere Processes in Organic Chemistry. Reaction of Trifluoromethyl Bromide with Electrochemically Generated Aromatic Anion Radicals and Sulfer Dioxide Anion Radicals", J. Am. Chem. Soc. 112, (1990), pp. 786-791.
Harzdorf, C. et al., "On perfluoroalkanesulfinic acids", Liebigs Ann. Chem., 1973, pp. 33-39.

* cited by examiner

*Primary Examiner* — Alicia L Otton
(74) *Attorney, Agent, or Firm* — Brinks Gilson & Lione

(57) ABSTRACT

The present invention relates to a process for the sulfinylation of a pyrazole derivative, characterized in that 5-amino-1-[2,6-dichloro-4-(trifluoromethyl)phenyl]-1H-pyrazole-3-carbonitrile (II) is reacted with a sulfinylating agent S in the presence of at least one amine acid complex wherein the amine(s) are selected from cyclic secondary amines and the acid(s) are selected from sulfonic acid derivatives, and with the addition of a halogenating agent, wherein S is [CF$_3$S(O)]$_2$O; or CF$_3$S(O)X wherein X means fluoro, chloro, bromo, iodo, a hydroxy group, or an alkaline or alkaline earth metal salt of the hydroxy group; or mixtures thereof.

13 Claims, No Drawings

PROCESS FOR THE SULFINYLATION OF A PYRAZOLE DERIVATIVE

This application is a National Stage application of International Application No. PCT/EP2007/061893 filed Nov. 5, 2007, which claims the benefit of U.S. Provisional Application Nos. 60/865,178 and 60/913,638, filed Nov. 10, 2006 and Apr. 24, 2007, respectively; the entire contents of all aforementioned applications are hereby incorporated herein by reference.

The present invention relates to a novel process for the sulfinylation of a pyrazole derivative, characterized in that 5-amino-1-[2,6-dichloro-4-(trifluoromethyl)phenyl]-1H-pyrazole-3-carbonitrile (II) is reacted with a sulfinylating agent S in the presence of at least one amine acid complex wherein the amine(s) are selected from cyclic secondary amines and the acid(s) are selected from sulfonic acid derivatives, and with the addition of a halogenating agent, wherein S is $[CF_3S(O)]_2O$; or $CF_3S(O)X$ wherein X means fluoro, chloro, bromo, iodo, a hydroxy group, or an alkaline or alkaline earth metal salt of the hydroxy group; or mixtures thereof.

The sulfinylation of a pyrazole-type compound refers to the substitution of a hydrogen atom on a pyrazole heterocycle carbon atom by an RS(=O)— group.

The direct sulfinylation of various organic molecules (not including pyrazole derivatives) employing a mixture of P(O)Cl$_3$ and $CF_3S(O)ONa$ has been described in T. Billard, A. Greiner, B. R. Langlois, Tetrahedron 55 (1999), p. 7243-7250. Likewise, C. Wakselman, M. Tordeux, C. Freslon, L. Saint-Jalmes, Synlett 2001, p. 550-552 teaches that direct sulfinylation of aromatic compounds takes place by $CF_3S(O)ONa$ or $CF_3S(O)OK$ in the presence of triflic acid $(CF_3S(O)_2OH)$.

Processes for the direct sulfinylation of 5-amino-1-[2,6-dichloro-4-(trifluoromethyl)phenyl]-1H-pyrazole-3-carbonitrile (II) have been described in EP-A 668 269, EP-A 1 331 222, CN-A 1374298, and in Y. Huilong, M. Zengeng, W. Shujuan, J. Hebei University of Science of Technology, Vol. 25(2), Sum 69 (2004), Serial no. 1008-1542 (2004) 02-0018-03.

In EP 668 269, the sulfinylation of 5-amino-1-[2,6-dichloro-4-(trifluoromethyl)phenyl]-1H-pyrazole-3-carbonitrile (II) with trifluoromethylsulfinic acid $CF_3S(O)OH$ and its derivatives $CF_3S(O)Cl$, $CF_3S(O)ONa$, $CF_3S(O)N(CH_3)_2$, or $CF_3S(O)N(CH_2CH_3)_2$ has been described. As chlorinating agent, phosgene, chloroformates, PCl$_5$ and SOCl$_2$ are mentioned. It is described that a reagent ("compound C") chosen from the group consisting of the tosylates, hydrochlorides and mesylates of a primary, secondary, or tertiary amine, preferably of dimethylamine, of pyridine, of trimethylamine, of diethylamine or of isopropylamine or gaseous hydrogen chloride, optionally in the presence of an equimolar amount of para-toluenesulfonic acid, may be added to complete the reaction. Examples are given for the following combinations of reactants:

$CF_3S(O)Cl$, dimethylamine p-tosylate;
$CF_3S(O)Cl$, pyridine hydrochloride salt;
$CF_3S(O)N(CH_3)_2$, p-toluolsulfonic acid, hydrochloric acid;
$CF_3S(O)Cl$, dimethylamine p-tosylate, hydrochloric acid; and
$CF_3S(O)ONa$, dimethylamine p-tosylate, SOCl$_2$.

The reactions carried out with $CF_3S(O)Cl$ as the sulfinylating agent give the highest yield of the final product.

The process described in CN-A 1374298 has been developed to overcome certain shortcomings of the process described in EP 668 269. CN-A 1374298 cites that $CF_3S(O)Cl$ is extremely unstable, $CF_3S(O)N(CH_3)_2$ and $CF_3SOOH$ are relatively difficult to prepare, that the reactivity $CF_3S(O)ONa$ is not high, and that the yield in the sulfinylation reaction is correspondingly relatively low. CN-A 1374298 describes the sulfinylation of 5-amino-1-[2,6-dichloro-4-(trifluoromethyl)phenyl]-1H-pyrazole-3-carbonitrile (II) with the potassium salt of trifluoromethylsulfinic acid, $CF_3S(O)OK$, or mixtures of the potassium and the sodium salt of trifluoromethylsulfinic acid, $CF_3S(O)OK$ with $CF_3S(O)ONa$, wherein the sulfinylating agent is combined with POCl$_3$, PCl$_3$, SOCl$_2$, COCl$_2$, or trichloromethylchloromethanoate. Optionally, the amine acid complex dimethylamine p-tosylate can be added to complete the reaction.

Examples are given for the following combinations of reactants $CF_3S(O)OK$; dimethylamine p-tosylate; POCl$_3$; and
$CF_3S(O)OK/Na$; dimethylamine p-tosylate; SOCl$_2$.

Huilong et al. describes the reaction of 5-amino-1-[2,6-dichloro-4-(trifluoromethyl)phenyl]-1H-pyrazole-3-carbonitrile (II) with the sodium salt of trifluoromethylsulfinic acid $(CF_3S(O)ONa)$, dimethylamine p-tosylate, and SOCl$_2$, with addition of catalytic amounts of DMF (dimethylformamide).

As described in EP-A 1 331 222, 5-amino-1-[2,6-dichloro-4-(trifluoromethyl)phenyl]-1H-pyrazole-3-carbonitrile (II) is sulfinylated using N-trifluoromethylsulfinylsuccinimide as the sulfinylating agent in the presence of triethylamine and without the addition of a chlorinating agent. The intermediate N-trifluoromethylsulfinylamino-pyrazole is isolated and under the conditions of a Thia-Fries rearrangement transformed into the final product 5-amino-1-[2,6-dichloro-4-(trifluoromethyl)phenyl]-4-(trifluoromethylsulfinyl)-pyrazole-3-carbonitrile.

Thus, the sulfinylation of 5-amino-1-[2,6-dichloro-4-(trifluoromethyl)phenyl]-1H-pyrazole-3-carbonitrile (II) to the final product product 5-amino-1-[2,6-dichloro-4-(trifluoromethyl)phenyl]-4-(trifluoromethylsulfinyl)-pyrazole-3-carbonitrile (common name: fipronil) has received considerable attention in the literature, the focus being on the optimization of the sulfinylating agent.

However, and also as cited in the recent review article "research progress on synthesis of fipronil and its main intermediates", Chinese Journal of Pesticides, 2004, Vol. 43, no. 12, 529-531, the sulfinylation of the pyrazole intermediate was still found not to be generally suitable for a large scale industrial production.

The reaction product of the present sulfinylation is fipronil, which is a market insecticide of considerable importance. Generally, technical manufacturing processes of pesticides have to fulfill high requirements with regard to yield and purity of the product, for reasons of profitability, but also, most important, in order to avoid the presence of potentially noxious side products. This is of special relevance for fipronil as it is also used in animal health products and therefore also comes into contact with companion animals.

It is also a legal requirement for technical manufacturing processes to avoid exposure of the plant employees but also of the environment to reagents which can have adverse effects to the health of the employees or environment. Therefore, it is desirable to have a technical manufacturing process at hand which avoids the use of gaseous reagents such as dimethylamine.

Furthermore, during the scale up of a process from the laboratory scale to a technical scale, problems may arise that were not as such or to the respective extend forseeable in the laboratory.

For example, the filling and/or dissolution of voluminous starting materials may take much longer on a big scale than in a small vessel, with the effect that the kinetic of the reaction is significantly changed, and thereby the conversion and the product spectrum.

Another example that can be mentioned is the appearance of side products that are, due to solubility or texture, difficult to separate from the desired main product on a large scale. Problems with extraction, filtration and clogging of filters may occurr. Insoluble starting materials or reaction (side) products may also challenge the agitation, heat dissipation or pumping thus leading to inhomogenous reaction mixtures.

Yet another challenge is the control of the course of the reaction temperature in large-scale processes. The temperature rates generally are lower which may have an influence on the side product spectrum. As high reaction temperatures and/or aggressive reaction media may cause corrosion, and also because of economic reasons, moderate reaction conditions (low temperatures) are preferred.

Hygroscopic properties of solids can complicate reactions that favorably are conducted under essentially water free conditions. For example, when the process as defined above is conducted using an amine acid complex wherein the acid is $H_2SO_4$—and not an acid as defined for the inventive process—the yield of the reaction is extremely poor.

Nonreactive catalysts are preferably used in the inventive process in order to avoid side reactions. Specific secondary or primary amines can react with the sulfinylating agent and form insoluble solids which give problems with stirring of the reaction mixture.

With a view to facilitating the work-up, reagents are preferably used that can be removed by distillation. Solids are removed by washing with acidic or alkaline solvents. It is not advantageous to employ reagents that have phase transfer catalytic properties which may hinder a phase separation during work-up.

Against this background and facing the fact that one of the essential starting materials for the current industrial production of fipronil is $CF_3Br$ (see e.g. WO 01/30760) which exhibits high environmental toxicity and is scheduled for production phase out by the Montreal Protocol on Substances that Deplete the Ozone Layer (it may then be used only as a feedstock material), it was an object of the present invention to develop a new, large scale industrial process for the manufacturing of fipronil which gives fipronil in high purity and yield while avoiding the use of dangerous reagents and avoiding problems with the technical reaction control.

Accordingly, the process defined at the outset was found. The obtained product fipronil is suitable for use as a pesticide for agricultural uses as well as non-crop uses for combating pests. Also, the obtained fipronil is suitable for use in the animal health field for combating animal health pests and parasites, especially for the long lasting protection against fleas and ticks on mammals.

Thus, the current invention also pertains to pesticidal or parasiticidal composition containing 5-amino-1-[2,6-dichloro-4-(trifluoromethyl)phenyl]-4-(trifluoromethylsulfinyl)-pyrazole-3-carbonitrile as prepared by the inventive process.

Likewise, the present invention relates to a method for the control of insects, acarids or nematodes by contacting the insect, acarid or nematode or their food supply, habitat, breeding ground or their locus with a pesticidally effective amount of 5-amino-1-[2,6-dichloro-4-(trifluoromethyl)phenyl]-4-(trifluoromethylsulfinyl)-pyrazole-3-carbonitrile prepared by the inventive process as well as to a method of protecting growing plants from attack or infestation by insects, acarids or nematodes by applying to the foliage or the seeds of the plants, or to the soil or water in which they are growing, a pesticidally effective amount of 5-amino-1-[2,6-dichloro-4-(trifluoromethyl)phenyl]-4-(trifluoromethylsulfinyl)-pyrazole-3-carbonitrile prepared by the inventive process. According to these methods, 5-amino-1-[2,6-dichloro-4-(trifluoromethyl)phenyl]-4-(trifluoromethylsulfinyl)-pyrazole-3-carbonitrile is usually applied in an amount of from 5 g/ha to 2000 g/ha.

Moreover, the present invention relates to a method for treating, controlling, preventing or protecting animals against infestation or infection by parasites which comprises orally, topically or parenterally administering or applying to the animals or their habitat a parasiticidally effective amount of 5-amino-1-[2,6-dichloro-4-(trifluoromethyl)phenyl]-4-(trifluoromethylsulfinyl)-pyrazole-3-carbonitrile prepared by the inventive process or its veterinarily acceptable enantiomers or salts.

Also, the present invention relates to a process for the preparation of a composition for treating, controlling, preventing or protecting animals against infestation or infection by parasites which comprises admixing 5-amino-1-[2,6-dichloro-4-(trifluoromethyl)phenyl]-4-(trifluoromethylsulfinyl)-pyrazole-3-carbonitrile prepared by the inventive process or its enantiomers or veterinarily acceptable salts with a veterinarily acceptable carrier. The composition may either be a concentrate or contains 5-amino-1-[2,6-dichloro-4-(trifluoromethyl)phenyl]-4-(trifluoromethylsulfinyl)-pyrazole-3-carbonitrile in a parasiticidally effective amount.

While there are examples given for certain amine acid complexes added at the beginning or during the course of the sulfinylation reaction, there is no teaching as to the crucial importance of the specific nature of the amine acid complex with regard to reaction control or to the yield and/or the purity of the final product fipronil.

In EP-A1 668 269, the following list of preferred amines is given: tosylates, hydrochlorides or mesylates of dimethylamine, pyridine, trimethylamine, diethylamine, isopropylamine. Experimental examples are described employing p-dimethylamine tosylate and pyridine hydrochloride as amine acid complexes.

Similarly, in both CN-A 1374298 and Huilong et al., examples are given for the use of dimethylamine p-tosylate as the amine acid complex.

However, as mentioned above, dimethyl amine, which is needed for the preparation of the dimethylamine p-tosylate, is particularly difficult to handle: it is a gas which is extremely flammable, harmful by skin contact and irritant to eye, skin and respiratory system. Thus, for large-scale processes, problems with regard to the environment from transportation as well as danger for plant employees have to be dealt with.

In none of the prior art documents, mention is made of the favorable use of cyclic secondary amines as amine(s) of the amine acid complex, with the acid(s) being selected only from sulfonic acid derivatives.

The novel subject of the present invention thus is a process for the sulfinylation of a pyrazole derivative, characterized in that 5-amino-1-[2,6-dichloro-4-(trifluoromethyl)phenyl]-1H-pyrazole-3-carbonitrile (II) is reacted with a sulfinylating agent S as defined hereinabove in the presence of at least one amine acid complex wherein the amine(s) are selected from cyclic secondary amines and the acid(s) are selected from sulfonic acid derivatives, and with the addition of a halogenating agent.

A reaction scheme may be depicted as follows:

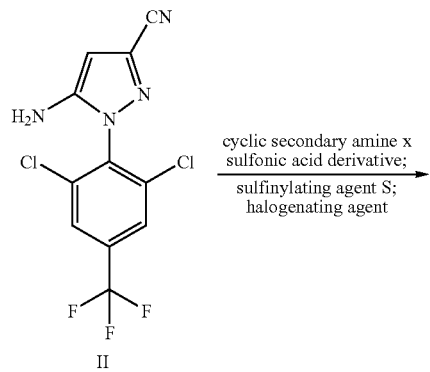

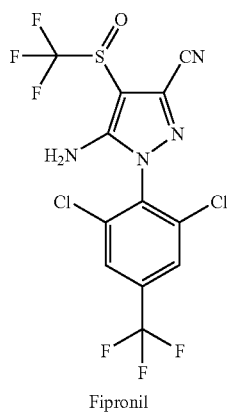

Fipronil

The sulfinylating agent is preferably selected from trifluoromethylsulfinylfluoride, trifluoromethylsulfinylchloride, trifluoromethylsulfinylbromide, trifluoromethylsulfinyliodide, trifluoromethylsulfinic acid, trifluoromethylsulfinic acid anhydride, trifluoromethylsulfinate sodium salt, trifluoromethylsulfinate potassium salt, and mixtures of these.

The sulfinylating agent is more preferably selected from trifluoromethylsulfinic acid, trifluoromethylsulfinic acid anhydride, trifluoromethylsulfinate sodium salt, trifluoromethylsulfinate potassium salt, and mixtures of these.

According to a preferred embodiment of the present invention, trifluoromethylsulfinylfluoride, trifluoromethylsulfinylchloride, trifluoromethylsulfinylbromide, or trifluoromethylsulfinyliodide, more preferably trifluoromethylsulfinylchloride, is used as the sulfinylating agent.

According to a preferred embodiment of the present invention, trifluoromethylsulfinate sodium salt is used as the sulfinylating agent.

According to another preferred embodiment of the present invention, trifluoromethylsulfinate potassium salt is used as the sulfinylating agent.

According to yet another preferred embodiment of the present invention, trifluoromethylsulfinic acid is used as the sulfinylating agent.

According to yet another preferred embodiment of the present invention, trifluoromethylsulfinic acid anhydride is used as the sulfinylating agent.

According to a preferred embodiment of the present invention, a mixture of the trifluoromethylsulfinate sodium and potassium salts, in a mixing ratio of from 0.01:99.99 weight % to 50:50 weight % is used as the sulfinylating agent.

Preferably, 1.0 to 1.35 molar equivalents, most preferably 1.2 molar equivalents, of the sulfinylating agent relative to 5-amino-1-[2,6-dichloro-4-(trifluoromethyl)phenyl]-1H-pyrazole-3-carbonitrile are used.

In a preferred embodiment, the sulfinylating agent is dried before its use until it is essentially water-free. "Water free" means that the content of water in the solid does not exceed 5 ppm to 100 ppm.

The halogenating agent is selected from thionylchloride, thionylbromide, phosphoroxychloride, oxalylchloride, phosgen, triphosgen $((CCl_3)_2C(=O))$, chloroformiates, phosphorpentachloride, phosphortrichloride, trichloromethylchloromethanoat, and xylenesulfonic acid chloride.

According to a preferred embodiment of the present invention, a chlorinating agent is used as the halogenting agent. Preferably, thionylchloride or phosphoroxychloride are used as the chlorinating agent.

According to another preferred embodiment of the present invention, phosphoroxychloride is used as the chlorinating agent.

Most preferably, thionylchloride is used as the chlorinating agent.

Preferably, 1.15 to 1.35 molar equivalents, most preferably about 1.2 molar equivalents, of the halogenating agent relative to 5-amino-1-[2,6-dichloro-4-(trifluoromethyl)phenyl]-1H-pyrazole-3-carbonitrile are used.

We have found that the choice of the amine acid complex plays a key role in the sulfinylation of 5-amino-1-[2,6-dichloro-4-(trifluoromethyl)phenyl]-1H-pyrazole-3-carbonitrile. Critical properties that influence the sulfinylating reaction are: steric (bulk) properties, pKs value, solubility, and molecular weight.

The sulfinylation reaction of the present invention is a one-pot synthesis of a two-step reaction. The first step involves the addition of the $CF_3S(O)-$ group to the amino group of the pyrazole ring. In a second step, fipronil is formed via a Thia-Fries rearrangement:

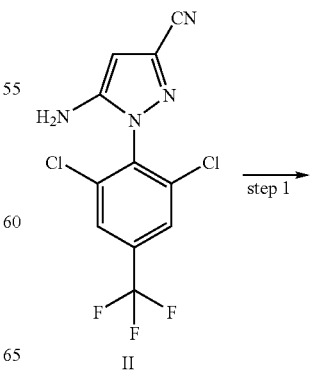

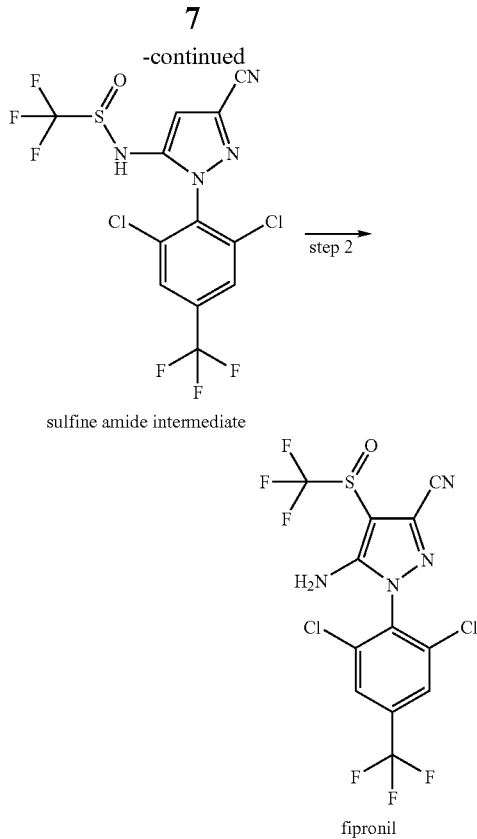

sulfine amide intermediate fipronil

The amine acid complex has two functions in this two-step reaction: (1) when sulfinylates are used as sulfinylating agents, it catalyzes the activation of the sulfinylate with the halogenating agent via intermediate formation of sulfinic acid. For this, catalytical amounts of 0.01 to 1.0 molar equivalents of amine acid complex relative to the pyrazole compound II are needed. (2) It accelerates the Thia-Fries rearrangement and has a significant influence on selectivity. With a view to obtain high yields and high purity, overall amounts of above 1 molar equivalents of amine acid complex relative to the pyrazole compound II are advantageously used for step two.

Preferred are amine acid complexes exhibiting low or essentially no hygroscopicity, as the sulfinylating process of the present invention advantageously is conducted in the essential absence of water (i.e. below 5 to 100 ppm of water).

Preferably, the cyclic secondary amines of the amine acid complex are defined by the formula $NHR^1R^2$ wherein $R^1$ and $R^2$ together with the nitrogen atom to which they are attached form a 3- to 10-membered saturated or partially unsaturated heterocyclic ring system, preferably a 5- to 6-membered saturated heterocyclic ring system, which is unsubstituted or substituted with 1 to 3 $C_1$-$C_8$-alkyl or $C_1$-$C_8$-haloalkyl groups, preferably with 1 to 3 $C_1$-$C_3$-alkyl or $C_1$-$C_3$-haloalkyl groups, most preferably with 1 to 3 $C_1$-$C_3$-alkyl groups, most preferably with 1 to 3 methyl groups, and which may contain 1 to 3 further heteroatoms selected from oxygen, nitrogen and sulphur, preferably from oxygen or nitrogen.

Preferred cyclic secondary amines are piperidine, piperidine which is substituted by $C_1$-$C_8$-alkyl or $C_1$-$C_8$-haloalkyl, preferably $C_1$-$C_2$-alkyl or $C_1$-$C_2$-haloalkyl, such as 2-methylpiperidine or 4-methylpiperidine, pyrrolidine, pyrrolidine which is substituted by $C_1$-$C_8$-alkyl or $C_1$-$C_8$-haloalkyl, such as 2-methylpyrrolidine or 3-methylpyrrolidine, imidazolidine, pyrrole, piperazine, or morpholine.

Especially preferred are morpholine, piperidine, or pyrrolidine.

Preferred acids of the amine acid complex for use in the present invention are sulfonic acid derivatives such as aromatic sulfonic acids, e.g. p-toluenesulfonic acid, benzenesulfonic acid, 4-ethyl benzenesulfonic acid, 4-chlorobenzenesulfonic acid, xylene sulfonic acid, 2,3-dimethylbenzene sulfonic acid, 2,4-dimethylbenzene sulfonic acid, 2,5-dimethylbenzene sulfonic acid, 2,6-dimethylbenzene sulfonic acid, 1-napthalenesulfonic acid, 2-napthalenesulfonic acid, mixtures of two or more of the isomers of dimethylbenzene sulfonic acids, or mesitylene sulfonic acid; or alkyl sulfonic acids, e.g. methane sulfonic acid or camphor sulfonic acid; or haloalkylsulfonic acids, e.g. trifluoromethylsulfonic acid. Especially preferred are acids with a pKs-value of below 2.

From the choice of amine acid complexes as used in the present invention, those with a pKa below 6, preferably 5, and above 10 are preferred.

Even more preferred acids are p-toluenesulfonic acid, xylene sulfonic acid, benzene sulfonic acid, methane sulfonic acid, trifluoromethyl sulfonic acid, or mesitylene sulfonic acid.

Most preferred acids are p-toluenesulfonic acid, xylene sulfonic acid, or benzene sulfonic acid.

Preferred amine acid complexes Q are listed in Table 1 which follows.

TABLE 1

| No. | Amine | Acid |
|---|---|---|
| Q-1 | Morpholine | p-toluene sulfonic acid |
| Q-2 | Morpholine | benzene sulfonic acid |
| Q-3 | Morpholine | xylene sulfonic acid |
| Q-4 | Morpholine | methane sulfonic acid |
| Q-5 | Morpholine | trifluoromethyl sulfonic acid |
| Q-6 | Piperidine | p-toluene sulfonic acid |
| Q-7 | Piperidine | benzene sulfonic acid |
| Q-8 | Piperidine | xylene sulfonic acid |
| Q-9 | Piperidine | methane sulfonic acid |
| Q-10 | Piperidine | trifluoromethyl sulfonic acid |
| Q-11 | Pyrrolidine | p-toluene sulfonic acid |
| Q-12 | Pyrrolidine | benzene sulfonic acid |
| Q-13 | Pyrrolidine | xylene sulfonic acid |
| Q-14 | Pyrrolidine | methane sulfonic acid |
| Q-15 | Pyrrolidine | trifluoromethyl sulfonic acid |
| Q-16 | Imidazole | p-toluene sulfonic acid |
| Q-17 | Imidazole | benzene sulfonic acid |
| Q-18 | Imidazole | xylene sulfonic acid |
| Q-19 | Imidazole | methane sulfonic acid |
| Q-20 | Imidazole | trifluoromethyl sulfonic acid |
| Q-21 | Imidazole | trifluoromethyl sulfonic acid |
| Q-22 | Pyrrole | p-toluene sulfonic acid |
| Q-23 | Pyrrole | benzene sulfonic acid |
| Q-24 | Pyrrole | xylene sulfonic acid |
| Q-25 | Pyrrole | methane sulfonic acid |
| Q-26 | Pyrrole | trifluoromethyl sulfonic acid |
| Q-27 | Piperazine | p-toluene sulfonic acid |
| Q-28 | Piperazine | benzene sulfonic acid |
| Q-29 | Piperazine | xylene sulfonic acid |
| Q-30 | Piperazine | methane sulfonic acid |
| Q-31 | Piperazine | trifluoromethyl sulfonic acid |

Amine acid complexes Q1, Q2, Q3, Q6, Q7, Q8 Q11, Q12, or Q13 are especially preferred.

With regard to their use in the inventive process, the combinations of sulfinylating agent and amine acid complex given in the tables below are especially preferred.

Table 2

Trifluoromethylsulfinate sodium salt is used as the sulfinylating agent, and the amine acid complex in each case is a row of table 1.

Table 3
Trifluoromethylsulfinate potassium salt is used as the sulfinylating agent, and the amine acid complex in each case is a row of table 1.

Table 4
Trifluoromethylsulfinic acid is used as the sulfinylating agent, and the amine acid complex in each case is a row of table 1.

Table 5
Trifluoromethylsulfinic acid anhydride is used as the sulfinylating agent, and the amine acid complex in each case is a row of table 1.

Table 6
A mixture of trifluoromethylsulfinate sodium and potassium salt in a mixing ratio of from 0.01:99.99 weight % to 50:50 weight % is used as the sulfinylating agent, and the amine acid complex in each case is a row of table 1.

Table 7
Trifluoromethylsulfinylfluoride is used as the sulfinylating agent, and the amine acid complex in each case is a row of table 1.

Table 8
Trifluoromethylsulfinylchloride is used as the sulfinylating agent, and the amine acid complex in each case is a row of table 1.

Table 9
Trifluoromethylsulfinylbromide is used as the sulfinylating agent, and the amine acid complex in each case is a row of table 1.

Table 10
Trifluoromethylsulfinyliodide is used as the sulfinylating agent, and the amine acid complex in each case is a row of table 1.

Also, in a further embodiment of the present invention, a Lewis acid such as $AlCl_3$, $FeCl_3$, $CaCl_2$, $ZnCl_2$, $BF_3$, $TiCl_4$, or $ZrCl_4$ can be used in exchange for the protonic acids cited above.

It can be advantageous to add the amine acid complex in two portions, one portion for step 1 and one portion after the addition of the pyrazole of formula II.

It can be advantageous to use two different amine acid complexes during the course of the reaction. For example, the first amine acid complex can be added in step 1 in amounts of 0.2 to 1 molar equivalents relative to pyrazole II, catalyzing the activation of the sulfinylate with the halogenating agent. After addition of the pyrazole of formula II, in step 2, the Thia-Fries rearrangement, a second amine acid complex different from the first one is added, in amounts of 0.2 to 1 molar equivalents relative to pyrazole II.

Preferably, 1.4 to 2.2 molar equivalents, most preferably 1.5 to 1.8 molar equivalents, of the amine acid complex according to the present invention relative to 5-amino-1-[2,6-dichloro-4-(trifluoromethyl)phenyl]-1H-pyrazole-3-carbonitrile are used.

When the sulfinylating agent is trifluoromethylsulfinic acid or a mixture containing trifluoromethylsulfinic acid, the molar amount of amine acid complex which is molar equivalent to the molar amount of trifluoromethylsulfinic acid is preferably generated in situ by addition of amine, and the remaining molar amount necessary to obtain the required 1.4 to 2.2 molar equivalents is added as amine acid complex.

In a preferred embodiment, the amine acid complex is dried before its use until it is essentially water-free. "Water free" means that the content of water in the solid does not exceed 5 ppm to 100 ppm.

Further additives can advantageously be added to the reaction mixture, such as potassium fluoride, pentafluorophenol, dimethylformamide, or 2,4-dinitrophenol. These additives are preferably added to the reaction mixture or solution or suspension of starting materials, respectively, before or at the reaction start. Most preferably, the additives are added at a low temperature of 5° C. to 10° C.

In a preferred embodiment, 0.1 to 1.5 molar equivalents of potassium fluoride relative to 5-amino-1-[2,6-dichloro-4-(trifluoromethyl)phenyl]-1H-pyrazole-3-carbonitrile are added to the reaction mixture or solution or suspension of starting materials, respectively, at 5° C. to 10° C. at or before the reaction start.

Is is advantageous to add pentafluorophenol, dimethylformamide, or 2,4-dinitrophenol in catalytic amounts or in 0.10 molar equivalents relative to 5-amino-1-[2,6-dichloro-4-(trifluoromethyl)phenyl]-1H-pyrazole-3-carbonitrile.

In a preferred embodiment, the additive is dried before its use until it is essentially water-free. "Water free" means that the content of water in the solid does not exceed 5 ppm to 100 ppm.

The reaction can be conducted in an inert organic solvent, preferably selected from
aliphatic, alicyclic or aromatic, optionally halogenated hydrocarbons such as aromatic organic hydrocarbons, e.g. toluene, xylene, trifluoromethylbenzene, benzene, nitrobenzene, monochlorobenzene, dichlorobenzene, and ethylbenzene, preferably toluene and xylene, most preferably toluene; or aliphatic or alicyclic, optionally halogenated hydrocarbons such as hexane, cyclohexane, benzine, 1,2 dichloroethane, dichloromethane, trichloromethane (chloroform), tetrachlorocarbon, preferably 1,2 dichloroethane, dichloromethane, trichloromethane; and
ethers, e.g. diethylether, dioxane, tetrahydrofuran, 2-methyl-tetrahydrofuran or ethylene glycol dimethyl- or diethylether; and
ketones, e.g. acetone or butanone; and
nitriles, e.g. acetonitrile or propionitrile; and
amides, e.g. dimethylformamide, DMI (1,3-dimethyl-2-imidazolidinon), dimethyllacetamide, N-methylformanilid, N-methylpyrrolidone or hexamethylphosphoric acid triamide; and
sulfoxides, e.g. dimethylsulfoxide.

In a preferred embodiment, solvents which are essentially water free are used. "Water free" means that the content of water in the solvent does not exceed 5 ppm to 100 ppm. The most preferred solvent is water free toluene.

The reaction is carried out under an inert gas atmosphere, such as under an argon or a nitrogen atmosphere.

In a preferred embodiment, a total of 3.0 to 8.0 molar equivalents, more preferably 4.0 to 7.5 molar equivalents, and most preferably 4.5 to 6.5 molar equivalents of the solvent relative to 5-amino-1-[2,6-dichloro-4-(trifluoromethyl)phenyl]-1H-pyrazole-3-carbonitrile are used. This relatively high concentration of starting materials maximizes the conversion to the sulfinamide intermediate.

In cases where the starting materials are dissolved and/or suspended, respectively, separately before their combination, about 25% to 40% of the solvent are employed for dissolving and/or suspending the 5-amino-1-[2,6-dichloro-4-(trifluoromethyl)phenyl]-1H-pyrazole-3-carbonitrile.

Generally, the sequence of addition of the starting materials 5-amino-1-[2,6-dichloro-4-(trifluoromethyl)phenyl]-1H-pyrazole-3-carbonitrile, amine acid complex, the sulfinylating agent and the halogenating agent generally can be freely chosen.

Preferably, the respective starting materials are dissolved or suspended, respectively, in the reaction solvent before addition to the reaction mixture.

The halogenating agent is preferably not added to 5-amino-1-[2,6-dichloro-4-(trifluoromethyl)phenyl]-1H-pyrazole-3-carbonitrile in the absence of the amine acid complex or the sulfinylating agent in the reaction mixture. In a preferred embodiment, the halogenating agent is dissolved in the solvent and added to a reaction mixture containing 5-amino-1-[2,6-dichloro-4-(trifluoromethyl)phenyl]-1H-pyrazole-3-carbonitrile, amine acid complex and the sulfinylating agent, all dissolved or suspended, respectively, in the solvent.

In a preferred embodiment, 5-amino-1-[2,6-dichloro-4-(trifluoromethyl)phenyl]-1H-pyrazole-3-carbonitrile (II) is combined with a mixture containing the sulfinylating agent, the amine acid complex and the halogenating agent. In this case, it can be advantageous to include a first portion (equaling about 1 molar equivalent relative to compound II) of halogenating agent in the mixture containing the sulfinylating agent, the amine acid complex and the halogenating agent and then to add the second portion (equaling about 0.1 to 0.2 molar equivalents relative to compound II) after addition of the compound II and stirring for approximately 30 to 60 minutes and shortly before rising the temperature to 30 to 50° C.

When the sulfinylating agent is trifluoromethylsulfinic acid, it is preferred to simultaneously add the trifluoromethylsulfinic acid and the halogenating agent to a solution or suspension of the amine acid complex, followed by addition of a solution of 5-amino-1-[2,6-dichloro-4-(trifluoromethyl)phenyl]-1H-pyrazole-3-carbonitrile to the reaction mixture.

In another preferred embodiment, a dissolved or suspended mixture of the sulfinylating agent, the amine acid complex and the halogenating agent in the solvent (preferably toluene) is cooled to about 3° C. to 10° C., and a solution of 5-amino-1-[2,6-dichloro-4-(trifluoromethyl)phenyl]-1H-pyrazole-3-carbonitrile in the solvent (preferably toluene) which as been heated to about 90° C. to 110° C. is combined with the cooled mixture.

In a preferred embodiment, after combination of 5-amino-1-[2,6-dichloro-4-(trifluoromethyl)phenyl]-1H-pyrazole-3-carbonitrile, the sulfinylating agent, the amine acid complex, and the chlorinating agent, the temperature is raised to 30° C. to 55° C. within 5 to 60 minutes.

It is also preferred to hold the reaction temperature initially at −20° C. to 10° C. for 5 to 60 minutes, preferably 20 to 40 minutes, followed by rising the temperature to 30° C. to 55° C. at a rate of 5° C./min to 45° C./min. Preferably, in order to obtain high purity products, the reaction mixture is raised to a temperature not above 35° C. When the sulfinylating agent is or contains $CF_3S(O)OH$, the initial reaction temperature preferably is −20° C. to 5° C., in case of trifluoromethylsulfinate alkaline or alkaline earth metal salts, the initial reaction temperature preferably is −5° C. to 10° C.

The reaction time depends upon the reaction temperature, the temperature control during the process, and the different reagents and solvents. The skilled artisan will be able to determine the appropriate reaction time in order to achieve the desired yield and purity. Typically, the reaction time will be about 5 to 15 hours, preferably 10 to 15 hours.

In a further preferred embodiment, the reaction is carried out in a pressure vessel at a pressure of 1.013 bar (1 atm) to about 4 bar.

After completion of the reaction, fipronil can be isolated by employing conventional methods such as quenching the reaction with hydrogen carbonates, such as $NaHCO_3$, carbonates such as $NaCO_3$, or hydroxides, such as NaOH, extracting fipronil with an unpolar organic solvent such as ethylacetate or methyl-tert.-butylether, washing the extract, e.g. with hydrogen carbonates such as $NaHCO_3$, concentrating the extract, e.g. in vacuo, crystallization of fipronil, and the like. The isolated fipronil can be purified by a technique such as chromatography, recrystallization and the like, if necessary.

The crystallization of the final product 5-amino-1-[2,6-dichloro-4-(trifluoromethyl)phenyl]-4-(trifluoromethylsulfinyl)-pyrazole-3-carbonitrile is typically conducted from a solution in a nonpolar, inert, preferably aromatic solvent with non-reactive substitutent such as chloro, fluoro, cyano, nitro, $C_1$-$C_8$-alkyl, or $C_1$-$C_8$-haloalkyl, particularly from a solution in benzene, ethylbenzene, monochlorobenzene, monofluorobenzene, 1,2-dichlorobenzene, 1,3-dichlorobenzene, 1,4-dichlorobenzene, toluene, o-xylene, m-xylene, p-xylene, styrene, i-propyl benzene, n-propyl benzene, 2-chlorotoluene, 3-chlorotoluene, 4-chlorotoluene, tert.-butyl benzene, sec.-butyl benzene, iso-butyl benzene, n-butyl benzene, 1,3-diisopropylbenzene, 1,4-diisopropylbenzene, 2-nitrotoluene, 3-nitrotoluene, 4-nitrotoluene, nitrobenzene, benzonitrile, mesitylene, trifluoromethyl benzene, 1,2-dichloroethane, acetonitrile, dimethylsulfoxide, tetrahydrofuran, acetone, alcohols such as methanol, ethanol, n-propanol, isopropanol, n-butanol, isobutanol, 2-butanol, or tert-butanol, preferably from a solution in monochlorobenzene, dichlorobenzene, ethylbenzene or toluene.

Preferably, the crystallization is done from monochlorobenzene.

Preferably, the crystallization is done from dichlorobenzene.

Preferably, the crystallization is done from ethylbenzene.

Preferably, the crystallization is done from toluene.

It can be advantageous to add about 1 to 30 percent of a polar solvent such as ketones, amides, alcohols, esters or ethers, preferably esters, ketones or ethers, such as acetone methyl ethyl ketone, pentan-2-one, diethylketone, 4-methyl-2-pentanone, 3-methyl-butan-2-one, tert-butyl-methyl-ketone, cyclohexanone, methylacetate, ethylacetate, isopropylacetate, N-butylacetate, isobutylacetate, diethylcarbonate, 2-butoxyethylacetate, dimethylformamide, dimethylacetamide, dimethylsulfoxide, nitromethane, nitroethane, water, ethanol, methanol, propan-1-ol, propan-2-ol, butan-1-ol, butan-2-ol, tert-butanol, 2-methyl-propan-1-ol, 2-methyl-propan-2-ol, pentan-3-ol, 2-methyl butan-1-ol, 3-methyl butan-1-ol, 1,2-ethanediol, 1,3-propandiol, 1,2-propandiol, cyclohexanol, dioxane, tetrahydrofurane, diethylether, methyl tert.-butyl ether, 2-methyl tetrahydrofuran, acetonitrile, propionitrile, or mixtures thereof.

In another embodiment, fipronil is crystallized from water, optionally with the addition of about 1 to 30 percent of a polar organic solvent.

Purification of the crude product can also be achieved via filtration over charcoal or silica or washing with water.

When obtained according to the inventive process, the obtained product fipronil in the crude reaction mixture before crystallization contains less than 3.0 weight %, calculated without solvent, of compound F, a typical, biologically active side product of fipronil syntheses.

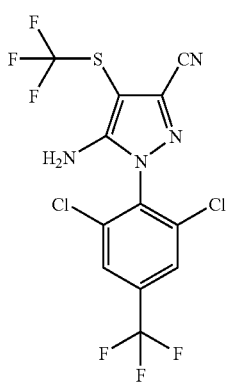

Compound F

After purification of the crude product by suitable methods such as washing and (re-) crystallizing, fipronil obtained by the inventive process contains less than 1.0 weight % of compound F.

Besides, the obtained product fipronil is free of the compound D which is a common side product of the currently large scale industrial process as described e.g. in WO 01/30760, even after purification. Fipronil when prepared by the inventive process in an inert atmosphere contains less than 300 ppm of compounds containing sulfur in its oxidation state (IV). It also is free of compound E which typically can appear as side product of the current industrial process.

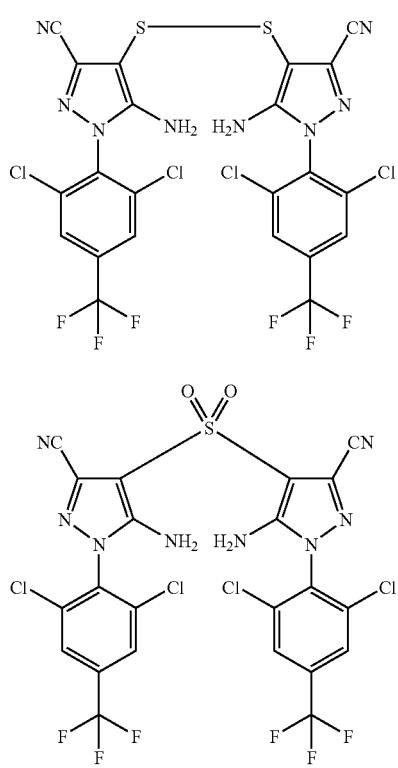

Compound D

Compound E

Furthermore, the obtained product fipronil is also free of trifluoroacetic acid, which is a reagent used in the current industrial process.

Moreover, when a chlorinating agent is used as the halogenating agent, the obtained fipronil product is practically free of bromine, meaning that is does not contain more than 5 to 20 ppm of bromine.

EXAMPLES

HPLCs were taken on a Hewlett Packard HP 1200, Chemstation, equipped with a J'Sphere ODS-H80, 4 μm, 4.6×250 mm (YMC) column, eluent A: 90 wt.-% water+10 wt.-% acetonitrile, eluent B: 10 wt.-% water+90 wt.-% acetonitrile, flow: 0.85 ml/min, detection: 235 nm,

|  |  | time [min] | | | | |
| --- | --- | --- | --- | --- | --- | --- |
|  |  | 0 | 2 | 17 | 25 | 35 |
| gradient: | A [%] | 60 | 60 | 25 | 0 | 0 |
|  | B [%] | 40 | 40 | 75 | 100 | 100. |

Yields given below are in mol percent of the obtained purified crystalline product after work-up. Purity is given in weight percent of the obtained solid.

Example 1

Sulfinylation of 5-amino-1-[2,6-dichloro-4-(trifluoromethyl)phenyl]-1H-pyrazole-3-carbonitrile with Morpholine Tosylate, Sodium Trifluoromethylsulfinate and Thionylchloride, in 6.5 Molar Equivalents of Toluene Within a 3-neck, 50 mL round bottom flask equipped with a magnetic stirrer bar and a thermometer were placed vacuum dried sodium trifluoromethylsulfinate (4.29 g, 27.5 mmol), vacuum dried morpholine tosylate (37.5 mmol), and 13 mL anhydrous toluene (6.5 molar equivalents relative to 5-amino-1-[2,6-dichloro-4-(trifluoromethyl)phenyl]-1H-pyrazole-3-carbonitrile) under an argon atmosphere. After cooling to 0° C. to 5° C. with an ice bath, thionylchloride (3.57 g, 30 mmol) was added slowly while keeping the reaction temperature below 5° C. After stirring for another 30 min, vacuum dried 5-amino-1-(2,6-dichloro-4-trifluoromethyl-phenyl)-1H-pyrazole-3-carbonitrile (8.03 g, 25 mmol, 99% purity) was added at 5° C., and the reaction mixture was heated to 50° C. within 5 min by a preheated water bath. The temperature of 50° C. was kept for another 6 hours before quenching the reaction with 50 mL of saturated NaHCO$_3$ solution.

The resulting suspension was diluted with 30 mL of ethylacetate. After phase separation the organic layer was washed once with saturated NaHCO$_3$ solution (crude yield in organic phase determined by quantitative HPLC: 72%) and concentrated under reduced pressure until dryness. The crude product was crystallized from refluxing toluene (100 g) affording the title compound as a white crystalline powder (66% yield, 97% purity by quantitative HPLC, 0.9 wt.-% compound F).

Example 2

Sulfinylation of 5-amino-1-[2,6-dichloro-4-(trifluoromethyl)phenyl]-1H-pyrazole-3-carbonitrile with Pyrrolidine Tosylate, Potassium Trifluoromethylsulfinate and Thionylchloride, in 6.5 Molar Equivalents of Toluene Within a 3-neck, 50 ml round bottom flask equipped with a magnetic stirrer bar and a thermometer were placed vacuum dried sodium trifluoromethylsulfinate (4.29 g, 27.5 mmol), vacuum dried pyrrolidine tosylate (37.5 mmol), and 13 ml anhydrous toluene (6.5 molar equivalents relative to 5-amino-1-[2,6-dichloro-4-(trifluoromethyl)phenyl]-1H-pyrazole-3-carbonitrile) under an argon atmosphere. After cooling to 0° C. to 5° C. with an ice bath, thionylchloride (3.57 g, 30 mmol) was added slowly while keeping the reaction temperature below 5° C. After stirring for another 30 min, vacuum dried 5-amino-1-(2,6-dichloro-4-trifluoromethyl-phenyl)-1H-pyrazole-3-carbonitrile (8.03 g, 25 mmol, 99% purity) was added at 5° C., and the reaction mixture was heated to 50° C. within 5 min by a preheated water bath. The temperature of 50° C. was kept for another 6 hours before quenching the reaction with 50 ml of saturated NaHCO$_3$ solution.

The resulting suspension was diluted with 30 ml of ethylacetate. After phase separation the organic layer was washed once with saturated NaHCO$_3$ solution (crude yield in organic phase determined by quantitative HPLC: 77%) and concentrated under reduced pressure until dryness.

The crude product was crystallized from refluxing toluene (100 g) affording the title compound as a white crystalline powder (68% yield, 96% purity by quantitative HPLC, 1.4 wt.-% compound F).

Example 3

Sulfinylation of 5-amino-1-[2,6-dichloro-4-(trifluoromethyl)phenyl]-1H-pyrazole-3-carbonitrile with Piperidine Tosylate, Potassium Trifluoromethylsulfinate and Thionylchloride, in 6.5 Molar Equivalents of Toluene The preparation was conducted as described above for example 2, affording the title compound as a white crystalline powder (76% crude yield, 68% yield after recrystallization, 96% purity by quantitative HPLC, 1.7 wt.-% compound F).

COMPARATIVE EXAMPLES

Secondary alkyl amines which form amine acid complexes with hydrofluoric or hydrochloric acid such as dimethylamine, diethylamine and diisopropylamie gave insoluble precipitates which remain with the product throughout the workup and recrystallization.

For a comparative example, diethylamine tosylate was chosen as amine acid complex as it has a somewhat related structure and molecular weight as some cyclic secondary amines according the present invention.

Example C1

Sulfinylation of 5-amino-1-[2,6-dichloro-4-(trifluoromethyl)phenyl]-1H-pyrazole-3-carbonitrile with Diethylamine Tosylate, Potassium Trifluoromethylsulfinate and Thionylchloride, in 6.5 Molar Equivalents of Toluene The preparation was conducted as described above for example 2, affording the title compound as a white crystalline powder (71% crude yield, 65% yield after recrystallization, 94% purity by quantitative HPLC, 1.8 wt.-% compound F).

Thus, in this experiment, it is demonstrated that the inventive process gives higher yields and higher purities as compared to the sulfinylation process described in the prior art.

The invention claimed is:

1. A process for the sulfinylation of 5-amino-1-[2,6-dichloro-4-(trifluoromethyl)phenyl]-1H-pyrazole-3-carbonitrile (II), consisting essentially of reacting the compound with a sulfinylating agent S in the presence of at least one amine acid complex wherein the amine(s) are cyclic secondary amines selected from the group consisting of piperidine, pyrrolidine, and morpholine, and the acid(s) are selected from the group consisting of p-toluenesulfonic acid, benzenesulfonic acid, and xylene sulfonic acid, and a halogenating agent selected from the group consisting of thionylchloride and phosphoroxychloride, wherein said sulfinylating agent S is selected from the group consisting of CF$_3$S(O)Cl, CF$_3$S(O)OH, [CF$_3$S(O)]$_2$O CF$_3$S(O)ONa, CF$_3$S(O)OK, and mixtures thereof wherein fipronil is obtained.

2. The process of claim 1, wherein said reaction is conducted in an organic solvent selected from the group consisting of toluene, benzene, xylene, trifluoromethylbenzene, monochlorobenzene, dichlorobenzene and ethylbenzene.

3. The process of claim 1, wherein said reacting comprises adding a solution of 5-amino-1-[2,6-dichloro-4-(trifluoromethyl)phenyl]-1H-pyrazole-3-carbonitrile to a mixture of said sulfinylating agent, said amine acid complex and said halogenating agent.

4. The process of claim 1, wherein 1.4 to 2.2 molar equivalents of said amine acid complex relative to 5-amino-1-[2,6-dichloro-4-(trifluoromethyl)phenyl]-1H-pyrazole-3-carbonitrile are present.

5. The process of claim 1, wherein 1.15 to 1.35 molar equivalents of said halogenating agent relative to 5-amino-1-[2,6-dichloro-4-(trifluoromethyl)phenyl]-1H-pyrazole-3-carbonitrile are used.

6. The process of claim 1, wherein 1.0 to 1.3 molar equivalents of said sulfinylating agent relative to 5-amino-1-[2,6-dichloro-4-(trifluoromethyl)phenyl]-1H-pyrazole-3-carbonitrile are present.

7. The process of claim 1, wherein said reacting comprises after combining of 5-amino-1-[2,6-dichloro-4-(trifluoromethyl)phenyl]-1H-pyrazole-3-carbonitrile, said sulfinylating agent, said amine acid complex, and said halogenating agent, the temperature is raised to 30° C. to 55° C., within 5 to 60 minutes.

8. The process of claim 1, wherein said reacting comprises after combining of 5-amino-1-[2,6-dichloro-4-(trifluoromethyl)phenyl]-1H-pyrazole-3-carbonitrile, said sulfinylating agent, said amine acid complex, and said halogenating agent, the temperature is raised to 30° C. to 39° C., within 5 to 60 minutes.

9. The process of claim 1, further comprising crystallizing 5-amino-1-[2,6-dichloro-4-(trifluoromethyl)phenyl]-4-(trifluoromethylsulfinyl)-pyrazole-3-carbonitrile from a solution of monochlorobenzene, dichlorobenzene, ethylbenzene or toluene.

10. The process of claim 1, further comprising admixing 5-amino-1-[2,6-dichloro-4-(trifluoromethyl)phenyl]-4-(trifluoromethylsulfinyl)-pyrazole-3-carbonitrile with a pesticidally acceptable carrier.

11. The process of claim 1, further comprising admixing 5-amino-1-[2,6-dichloro-4-(trifluoromethyl)phenyl]-4-(trifluoromethylsulfinyl)-pyrazole-3-carbonitrile with a veterinarily acceptable carrier.

12. The process of claim 1, wherein the process yields less than 10 ppm of the compound D
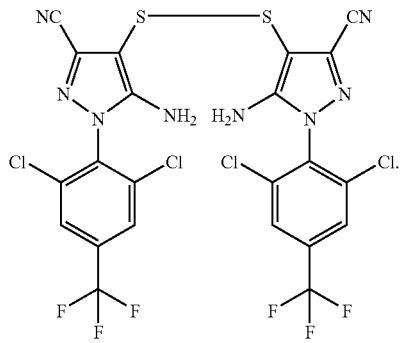
Compound D
13. The process of claim 1, wherein the process yields less than 3% by weight of the compound F:
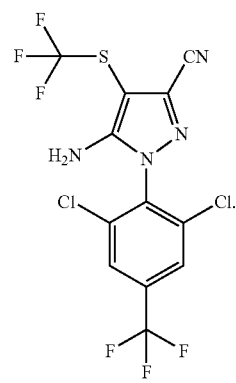
Compound F
* * * * *